United States Patent [19]

Rossi

[11] Patent Number: 4,874,853

[45] Date of Patent: Oct. 17, 1989

[54] SYNTHETIC OLIGONUCLEOTIDES USEFUL IN DIAGNOSIS OF CHRONIC MYELOGENOUS LEUKEMIA

[75] Inventor: John J. Rossi, Glendora, Calif.

[73] Assignee: City of Hope, Duarte, Calif.

[21] Appl. No.: 182,434

[22] Filed: Apr. 18, 1988

[51] Int. Cl.[4] ............................................. C07H 21/04
[52] U.S. Cl. ........................................ 536/27; 536/28; 536/29; 935/78; 435/6
[58] Field of Search ............................. 536/27, 28, 29

[56] References Cited

PUBLICATIONS

Jeffreys, Chem. Abstr. (Patent) CA 106: 29695y.
Brierley et al, Nuclei Acids Research, v. 13, pp. 485-500 (1985).
Matsutani et al., J. Mol. Biol., v. 196, pp. 445-455 (1987).
Barker et al., Chem. Abstr. (Patent) CA 103: 99737a (1095).
Hobart et al., Nature, v. 288, kpp. 137-141 (1980).

Primary Examiner—Ronald W. Griffin
Assistant Examiner—L. Eric Crane
Attorney, Agent, or Firm—Edward S. Irons

[57] ABSTRACT

Synthetic oligonucleotide for detection of the bcr-abl RNA from blood or bone marrow of patients with chronic myelogenous leukemia.

4 Claims, No Drawings ures. Pursuant
SYNTHETIC OLIGONUCLEOTIDES USEFUL IN DIAGNOSIS OF CHRONIC MYELOGENOUS LEUKEMIA

BACKGROUND OF THE INVENTION

Chronic myelogenous leukemia is characterized by a reciprocal translocation between chromosomes 9 and 22 of man. This results in an abbreviated chromosome 22 termed the Philadelphia chromosome which is found in over 95 percent of patients with chronic myelogenous leukemia and in a minority of patients with acute lymphoblastic leukemia. In this translocation, the abl gene from chromosome 9 is spliced to a region on chromosome 22 called the breakpoint cluster region (bcr). This fusion gene, bcr-abl, is transcribed into a unique RNA transcript that is about 8 kb in size.

DESCRIPTION OF THE INVENTION

This invention pertains to primers and probes which can detect the bcr-abl RNA from blood or bone marrow of patients with chronic myelogenous leukemia. The patient's RNA is amplified using unique primers homologous to flanking sequences to the bcr-abl splice sites. Oligonucleotide probes complementary to the two most common bcr-abl splice sequences are then used to detect the amplified DNA. The assay is useful to detect residual or relapsed chronic myelogenous leukemia and to distinguish between Philadelphia chromosome positive acute lymphoblastic leukemia and lymphoid blast crisis of chronic myelogenous leukemia.

More particularly, the positions of the break points between the two genetic loci involved in the translocation (bcr and abl) are variable, but the fused genes produce two different, but distinct chimeric mRNA's which code for a fusion protein with an enhanced protein kinase activity. The primary transcript from this novel gene fusion is very large, while messenger splicing events pare this down to an 8.5 kilobase mRNA with a unique splice joint matching bcr exons 1,2 with abl exon 2, or bcr exons 1,2,3 with abl exon 2 and the remainder of the abl downstream sequences. Pursuant to this invention, synthetic DNA probes have been developed specifically to detect the CML bcr-abl fusion mRNA. In addition, this invention involves two synthetic oligodeoxyribonucleotide primers, one complementary to a sequence in bcr exon 2, while the other is complementary to a sequence in abl exon 2. Beginning with less than one microgram of cells, the sequences including and in between the two primers are amplified, and the synthetic oligonucleotide probes are used to detect the amplified products (which are derived either from a splice which joined bcr 1,2 with abl 2, or bcr 1,2,3 with abl 2). The sequences of the probes and the positions in the fusion message are present below.

```
bcr  exon  2                              / bcr   exon   3
CAC AGC ATT CCG CTG ACC ATC AAT AAG GAA G/AT GAT GAG TCT CCG GGG
5*************************bcr  primer
CTC TAT GGG TTT CTG AAT GTC ATC GTC CAC TCA GCC ACT GGA TTT AAG
        /< unique  fusion  point  abl  exon  2
CAG AGT TCA A/AA GCC CTT CAG CGG CCA GTA GCA TCT GAC TTT GAG CCT
CAG GGT CTG AGT GAA GCC GCT CGT TGG AAC TCC AAG GAA AAC CTT CTC
                                                    g gaa gag
                                                    *********
GCT GGA CCC AGT G
c g a  c c t  g g g  t c a  c5' abl primer
******************
```

Detection probes for bcr 3 /abl 2 splice junction = 5'CTGAAGGGCTTTTGAACTCT 3'
    abl        /     bcr     3 for bcr 2 /abl 2 splice junction = 5'CCGTGAAGGGCTTCTTCCTTATTG 3'
    abl         /       bcr     2

I claim:

1. A synthetic oligonucleotide useful as a probe to detect the chronic myelogenous leukemia bcr-abl fusion mRNA, said synthetic oligonucleotide including the sequence:
   5'CTGAAGGGCTTTTGAACTCT 3' or the sequence
   5'CCGTGAAGGGCTTCTTCCTTATTG3'.

2. A synthetic oligonucleotide including the sequence

5' CTGAAGGGCTTTTGAACTCT 3'
       abl       /    bcr    3 or the sequence

5' CCGTGAAGGGCTTCTTCCTTATTG 3'.
       abl        /      bcr     2

3. A synthetic oligonucleotide including the sequence 5'CTGAAGGGCTTTTGAACTCT 3'.

4. A synthetic oligonucleotide including the sequence 5'CCGTGAAGGGCTTCTTCCTTATTG 3'.

* * * * *